United States Patent [19]
Schultze et al.

[11] Patent Number: 5,677,446
[45] Date of Patent: Oct. 14, 1997

[54] POLYAZACYCLOALKANE COMPOUNDS

[75] Inventors: Lisa Schultze; Al Ray Bulls, both of Wayne, Pa.

[73] Assignee: Nycomed Imaging AS, Oslo, Norway

[21] Appl. No.: 478,754

[22] Filed: Jun. 7, 1995

[30] Foreign Application Priority Data

Mar. 10, 1995 [GB] United Kingdom ............... 9504910

[51] Int. Cl.$^6$ ............................................. C07D 257/00
[52] U.S. Cl. ............................................. 540/474; 540/467
[58] Field of Search ............................................. 540/474

[56] References Cited

U.S. PATENT DOCUMENTS

| | | | |
|---|---|---|---|
| 5,064,956 | 11/1991 | Kruper, Jr. | 540/474 |
| 5,271,927 | 12/1993 | Parker et al. | 424/9 |
| 5,364,614 | 11/1994 | Platzek et al. | 540/474 |
| 5,380,515 | 1/1995 | Winchell et al. | 424/9 |
| 5,424,423 | 6/1995 | Uggeri et al. | 540/474 |
| 5,434,262 | 7/1995 | Guilabd et al. | 540/474 |
| 5,536,491 | 7/1996 | Asai et al. | 540/465 |

FOREIGN PATENT DOCUMENTS

| | | |
|---|---|---|
| 0 232 751 | 1/1987 | European Pat. Off. . |
| 0 292 689 | 4/1988 | European Pat. Off. . |
| WO 89/01476 | 8/1988 | WIPO . |

OTHER PUBLICATIONS

Jerald S. Bradshaw et al., "New High Yield Syntheses of Cyclams using the Crab–Like Cyclization Reaction", Tetrahedron Letters, vol. 31, No. 8., pp. 1077–1080.

F. Wagner et al., "N–Alkylation of Macrocyclic Secondary Amine Complexes of Nickel (II)", Inorganic Chemistry, vol. 15, No. 2, 1976, pp. 408–417.

J. F. Pilichowski et al., "Synthese de Coordinats Macrocycliques Polyazotes Comportant Une Fonction Amine Secondaire Discriminee", Tetrahedron, vol. 41, No. 10. pp. 1959 to 1964, 1985.

D. D. Dischino et al., "Synthesis of Nonionic Gadolinium Chelates Useful as Contrast Agents for Magnetic Resonance Imaging", Inorg. Chem. 1991, 30, 1265–1269.

William J. Kruper, Jr., et al., "Unexpected Selectivity in the Alkylation of Polyazamacrocycles", J. Org. Chem. 1993, 58, 3869–3876.

Aza–Crown Macrocycles vol. 51., Bradshaw et al., Chapter VII, p. 351, 1993., John Wiley & Sons, Inc.

*Primary Examiner*—Mukund J. Shah
*Assistant Examiner*—Pavanaram K. Sripada
*Attorney, Agent, or Firm*—Fish & Richardson P.C.

[57] ABSTRACT

The present invention relates to tribenzylcyclen compounds of formula I

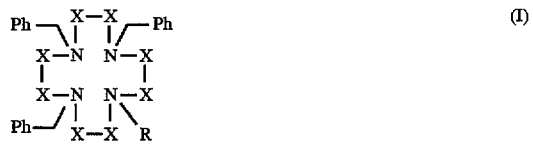

(where R is hydrogen, or a $C_{1-12}$ alkyl group optionally substituted by hydroxy, alkoxy or aryl groups or R is an amphiphilic aralkyl group comprising a N, S, O or P interrupted $C_{2-25}$ alkylene chain, e.g. a polyalkylene oxide chain or R provides a bridge to a second tribenzylcyclen group, but with the proviso that R is other than benzyl; X is $CHR_1$, or where R is hydrogen two X groups may each represent CO groups; and $R_1$ is hydrogen, a $C_{1-6}$ alkyl group optionally substituted by hydroxy, alkoxy or carboxy groups or an aralkyl group having 1 to 6 carbons in the alkyl moiety and optionally. substituted in the aryl moiety by alkyl, alkoxy, hydroxy or isothiocyanate groups). These compounds are useful in the preparation of DO3A, N-substituted-1,4,7,10-tetraazacyclododecane-N',N",N"'-triacetic acids, and the phosphonic acid analogs.

4 Claims, No Drawings

POLYAZACYCLOALKANE COMPOUNDS

FIELD OF THE INVENTION

This invention relates to novel polyazacycloalkane compounds, to processes for their preparation and to their use in the production of macrocyclic chelating agents.

BACKGROUND OF THE INVENTION

In the field of diagnostic medical imaging, complexes of paramagnetic metal ions are widely used as contrast agents. The lanthanide metal ions, especially Gd(III) and Dy(III) are among the most effective MR contrast enhancers and to ensure appropriate biodistribution and post-contrast bioelimination, they are administered in chelate complexes which have very high stability constants. While some of the chelating agents used have a linear polyamine structure (eg. DTPA as in Schering's GdDTPA product Magnevist and DTPA-BMA as in Nycomed Imaging's GdDTPA-BMA product Omniscan), others have a macrocyclic polyamine structure, eg. DOTA as in Guerbet's GdDOTA product Dotarem and HP-D03A as in Squibb's GdHP-D03A product ProHance.

The 1,4,7,10-tetraazacyclododecane (cyclen) polyamine skeleton of DOTA and HP-D03A forms the basis for a range of particularly stable lanthanide-chelating macrocyclic chelants in which three or four of the ring nitrogens carry a pendant, ionizable metal coordinating group, eg. a carboxylic or phosphonic acid group. Since the lanthanide ions of interest are generally in the III state, cyclen-based chelants carrying three such acid groups offer the opportunity to produce charge-neutral or non-ionic chelate complexes. This is of importance since various side effects of contrast agent compositions are associated with hypertonicity and non-ionic contrast agents have a lower contribution to the overall osmolality of the composition.

Recently, Schering and Nycomed Salutar have proposed various "dimeric" macrocyclic chelates in the chelant for which two cyclen rings are linked by a bridge between ring nitrogens. The remaining ring nitrogens in these chelants will generally carry metal coordinating acid groups so that the resultant complex carries two metal ions but again is charge-neutral overall.

Cyclen is a key intermediate in the preparation of such macrocyclic chelating agents, with the ring nitrogens being appropriately substituted after macrocyclic ring formation has occurred.

Thus for example one may produce DOTA (1,4,7,10-tetraazacyclododecane-N,N',N'',N'''-tetraacetic acid) by reacting cyclen with bromo-acetic acid or its t-butyl ester, in the later case followed by ester cleavage.

Where however one of the ring nitrogens is to carry a different substituent from the other three, use of cyclen leads to yield loss due to the formation of undesired N-substitution products. One approach to this is to mono-substitute cyclen before substituting the three remaining nitrogens; another is to start from a mono-substituted cyclen produced for example by condensing a triamine with a monoamine, with one of the two amine reagents carrying the substituent group (eg. as in the N-monosubstituted cyclen Syntheses of Dischino et al., Inorg Chem. 30: 1265 (1991), Pilchowski et al Tetrahedron41: 1956 (1981), and Tweedle et al. (EP-A-232 751 and EP-A-292689)).

The present invention is based on the finding that, for the production of chelating agents comprising triacid substituted cyclen, a particularly straightforward and flexible route is offered via the N,N',N''-tribenzylcyclens, compounds which are themselves novel.

SUMMARY OF THE INVENTION

Thus in one aspect the invention provides tribenzylcyclen compounds of formula I

(where R is hydrogen, or a $C_{1-12}$ alkyl group optionally substituted by hydroxy, alkoxy or aryl groups or R is an amphiphilic aralkyl group comprising a N, S, O or P interrupted $C_{2-25}$ alkylene chain, e.g. a polyalkylene oxide chain or R provides a bridge to a second tribenzylcyclen group, but with the proviso that R is other than benzyl; X is $CHR_1$, or where R is hydrogen two X groups may each represent CO groups; and $R_1$ is hydrogen, a $C_{1-6}$ alkyl group optionally substituted by hydroxy, alkoxy or carboxy groups or an aralkyl group having 1 to 6 carbons in the alkyl moiety and optionally substituted in the aryl moiety by alkyl, alkoxy, hydroxy or isothiocyanate groups).

DETAILED DESCRIPTION OF THE INVENTION

In formula I, any alkyl or alkylene moiety unless otherwise specified conveniently contains 1 to 12, preferably 1 to 6, carbons and any aryl group is preferably an optionally substituted phenyl group.

One example of an amphiphilic chain R group is a group L-Ar(—AH)$_n$ where each L is an $C_{2-25}$-alkylene linker wherein at least one $CH_2$ moiety is replaced by $X^1$ or a group $X^1(CH2CH_2X^1)_u$ (where u is a positive integer) such as $X^1CH_2CH_2X^1$, $X^1CH_2CH_2X^1CH_2CH_2X^1$, $X^1CH_2CH_2X^1CH_2CH_2X^1CH_2CH_2X^1$, etc), and wherein L is optionally interrupted by a metabolizable group M but with the provisos that the terminus of L adjacent the cyclen ring is $CH_2$ and that the terminus of L adjacent Ar is $X^1$ or a $CH_2$ group adjacent or separated by one $CH_2$ from a group $X^1$ (thus for example the L-Ar linkage may be $L^1-X^1$-Ar, $L^1$-$CH_2$-Ar, $L^1$-$X^1CH_2$-Ar or $L^1$-$X^1CH_2CH_2$-Ar, where $L^1$ is the residue of L);

each Ar is an aryl ring optionally substituted by or having fused thereto a further aryl ring;

each AH is a protic acid group, preferably an oxyacid, e.g. a carbon, sulphur or phosphorus oxyacid or a salt thereof;

each $X^1$ is O, S, $NR_2$ or $PR_2$;

each $R_2$ is hydrogen, alkyl or aryl;

and n is a positive integer for example 1, 2 or 3.

Where in the compound of formula I, carbonyl X groups are present, eg. as in the case where the compound is produced by a cyclization involving amines having N-attached $LvCOCH_2$ or $LvCH_2CO$ groups (where Lv is a leaving group such as a halogen atom), the compound can readily be reduced to the analogous compound of formula I wherein all X groups are $CH_2$.

The compounds of formula I wherein R is hydrogen my readily be prepared by diamine:diamine or monoamine: triamine cyclizations. If any carbonyl groups are present these can be reduced and the tribenzyl cyclen product can then be reacted to introduce a non-hydrogen R group. Debenzylation and carboxymethylation or phosphonomethylation then yield an R-DO3A compound (or the phosphonic acid equivalent) which can if desired be further converted to desired DO3A compounds by deprotection or removal of the R group followed if desired by substitution of the free ring nitrogen with a desired end group.

Particular benefits of the invention lie in the selectivity of the debenzylation stage, the higher yields, the greater ease of isolation of the macrocyclic end product and the significantly greater ease of performance on a commercial level of debenzylation than of the detosylation required for example in the substituted-DO3A syntheses of Tweedle et al. (supra).

Viewed from a further aspect the invention provides the use of compounds of formula I for the preparation of DO3A, N-substituted-1,4,7,10-tetraazacyclododecane-N,,N',N'''-triacetic acids, and the phosphonic acid analogs.

Viewed from a still further aspect the invention provides a process for the preparation of a compound of formula I, said process comprising at least one of the following steps:

(a) reacting a diamine of formula II

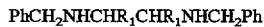
PhCH$_2$NHCHR$_1$CHR$_1$NHCH$_2$Ph (II)

with a diamine of formula III

YN(CH$_2$Ph)CHR$_1$CHR$_1$NHY (III)

(where Y is CH$_2$COLv or COCH$_2$Lv and Lv is a leaving group, eg. a halogen atom or an OTs Or OMs group) to yield a compound of formula IV or V

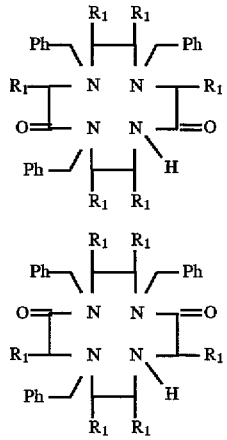

(IV)

(V)

(b) reacting a triamine of formula VI

Z$_1$NHCHR$_1$CHR$_1$N(Z$_2$)CHR$_1$CHR$_1$NHZ$_3$ (VI)

with a monoamine of formula VII

Z$_4$N(CHR$_1$COLv)$_2$ (VII)

to yield a compound of formula VIII

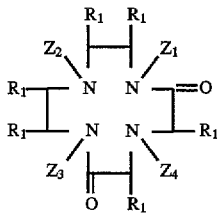

(VIII)

(wherein one of Z$_1$, Z$_2$, Z$_3$, and Z$_4$ is a hydrogen atom and the others are benzyl groups);

(c) reducing a compound of formula IV, V or VIII to yield a compound of formula IX

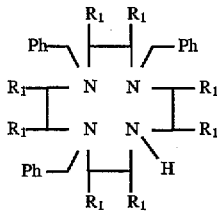

(IX)

(d) reacting a compound of formula IX with a compound of formula X

Lv-R$^1$ (X)

(where Lv is a leaving group (eg. a halogen atom or an Ms or OTs group) and R$^1$ is a group R other than hydrogen or where Lv-R$^1$ is a cyclic or unsaturated compound (eg. an epoxide) nucleophilically substitutable by an amine nitrogen to yield an N-attached R group other than hydrogen);

(e) reacting a monoamine of formula XI

LvCHR$_1$CHR$_1$NR$^2$CHR$_1$CHR$_1$Lv (XI)

(where R$^2$ is a group R or a nitrogen protecting group, eg. Ms) with a triamine of formula VI, and if required deprotecting the R$^2$-substituted nitrogen in the resulting tribenzylcyclen.

The reagents of formulae II and VI can be prepared by reaction of ethylenediamine or diethylenetriamine with a benzylating agent, eg. a compound PhCH$_2$Lv or with benzaldehyde followed by catalytic reduction of the imino product.

The reagent of formula III may be prepared by benzylating ethylenediamine, eg. as described for the compounds of formulae I and VI, and acylating the benzylamine product, eg. by reaction with chloroacetylbromide or bromoacetylchloride or other haloacetylhalides or comparable doubly-activated acetic acid reagents.

The iminodiacetic acid derivatives of formula VII can be prepared by conventional carboxylic acid activation procedures.

The amine substitution and carbonyl reduction reactions of steps (c) and (d), may be performed by conventional means as can the deprotection stages which may be required.

Subsequent reaction of the compounds of formula I wherein each X is CHR$_1$ can be performed using standard amine substitution and debenzylation procedures. Debenzylation will preferably be effected by catalytic hydrogenation, eg. at a hydrogen pressure of 10 to 1000 psi, preferably 30–200 psi, a temperature of 0° to 200° C., preferably 25° to 120° C., and over a conventional hydrogeneration catalyst such as palladium/charcoal or platinum/C. Debenzylation is described by Rylander in "Catalytic hydrogeneration over platinum metals" Academic Press, 1967, pages 449 to 468.

By contrast the detosylation reaction used by earlier workers to pass from N-substituted-N',N",N'"-tritosylcyclen to N-substituted cyclen generally required treatment with concentrated sulphuric acid at 100° C. for 24 hours. On a commercial scale such high acid concentration conditions and long reaction times are highly disadvantageous.

Loading of acid groups, eg. carboxymethyl or phosphonomethyl groups, onto the debenzylated cyclen can again be effected using conventional procedures, eg. reaction with bromoacetic acid, t-butyl-bromoacetate or by reaction with formaldehyde and phosphorous acid followed where necessary by removal of any protecting groups and amidation if desired.

Thus the invention provides improved routes for high yield production of cyclen tri-substituted by acid groups and optionally mono-substituted by a desired further group, eg. DO3A HP-DO3A, or other hydroxyalkyl-DO3As, as well as DO3A—DO3A dimers.

Analogously one may use a diamine:diamine or monamine:triamine condensation to produce N-benzylcyclen, substitute the three vacant, ring nitrogens, debenzylate and if desired substitute the vacant ring nitrogen to produce such mono/tri-hetero-substituted cyclens. Thus viewed from this aspect the invention also provides a process for the production of DO3A or DO3A analog chelating agents, said process comprising the following steps (1) (a) reacting a diamide of formula XII

Z$_1$NHCHR$_1$CHR$_1$NH$_2$      (XII)

with a diamine of formula XIII

YNZ$_2$CHR$_1$CHR$_1$NHY      (XIII)

(where R$_1$ and Y are as defined above, and one of Z$_1$ and Z$_2$ is hydrogen and the other is a benzyl group),
or (b) reacting a triamine of formula XIV

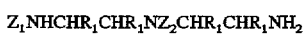

Z$_1$NHCHR$_1$CHR$_1$NZ$_2$CHR$_1$CHR$_1$NH$_2$      (XIV)

with a monoamine of formula XV or XVI

Z$_3$N(CH$_2$COLv)$_2$      (XV)

Z$_3$N(CHR$_1$CHR$_1$Lv)$_2$      (XVI)

(where R$_1$ and Lv are as previously defined, one of Z$_1$, Z$_2$ and Z$_3$ is a benzyl group and the other two are hydrogen atoms),
and (c) where necessary reducing the cyclic dione thus produced to yield N-benzyl-cyclen;
(2) reacting the N-benzyl-cyclen to introduce acid groups (e.g. carboxymethyl or phosphonomethyl groups) at the unsubstituted ring nitrogens;
(3) debenzylating the N-acid substituted product; and
(4) if desired, N-alkylating the debenzylated product, e.g. to introduce a hydroxy-alkyl group.

Following production of the macrocyclic tetraazacycloalkanes according to the process of the invention, and if necessary the reduction of any ring carbonyl groups, the products will generally be subjected to N-alkylation in order to produce the desired chelating agents. The N-alkylation step to introduce desired alkyl or substituted alkyl groups onto the macrocyclic skeleton can be performed using conventional alkylation techniques, for example involving reaction with an alkylhalide R$^2$-Hal (where Hal is a halogen atom such as chlorine or bromine and R$^2$ is an alkyl group optionally substituted, for example by hydroxy or alkoxy groups or by chelant moieties, such as carboxyamide groups or carboxyl or phosphonic acid groups (optionally protected by ester groups)). The alkyl moiety in R$^2$ will conveniently contain 1 to 12 carbon atoms and any chelant moiety will preferably be on the alpha or beta carbon. If a protected chelant group is introduced in this fashion, it may subsequently be deprotected, for example by ester cleavage to make the group available for metallation.

The macrocyclic chelating agents can be used in metallated or unmetallated forms. In the latter case they may for example be used as therapeutic agents, eg in the treatment of cancer.

Metallation of the macrocyclic chelating agent may be effected by conventional methods, for example as described in the patent literature relating to MR contrast agents (see for example EP-A-71564, EP-A-130934, EP-A-165728, EP-A-258616, WO-A-86/06605, etc.).

The choice of metal ions to be complexed will depend upon the intended end use for the chelate complex. Especially preferred are ions of metals of atomic numbers 22 to 32, 42 to 44, 49 and 57 to 83, in particular Gd.

Where the chelate is to be used as an MR contrast agent, the chelated metal species is conveniently a paramagnetic ion of a transition metal or a lanthanide, preferably having an atomic number of 21 to 29, 42, 44 or 57 to 71. Complexes of Eu, Gd, Dy, Ho, Cr, Mn and Fe are especially preferred and Gd$^{3+}$, Mn$^{2+}$ and Dy$^{3+}$ are particularly preferred ions. For use as contrast agents in MRI, the paramagnetic metal species is conveniently non-radioactive as radioactivity is a characteristic which is neither required nor desirable.

Where the chelate complex is to be used as an X-ray or ultrasound contrast agent, the metal is preferably a heavy metal such as a non-radioactive metal with an atomic number greater than 37, preferably greater than 50, for example Dy$^{3+}$.

Where the metal complex is to be used in scintigraphy or radiotherapy, the chelated metal species must of course be radioactive and any conventional complexable radioactive isotope, such as $^{99m}$Tc or $^{111}$In for example may be used. For radiotherapy the chelated metal may for example be $^{153}$Sm, $^{67}$Cu or $^{90}$Y.

All publications referred to herein are incorporated herein by reference.

Embodiments of the invention will now be described with reference to the following non-limiting Examples.

EXAMPLE 1

N-benzylethylenediamine 1 and N,N'-dibenzylethylenediamine 2

(a) Benzylchloride and ethylenediamine are reacted together in 1:1 or 2:1 mole ratios in the presence of sodium hydroxide to yield 1 and 2, respectively.

(b) Benzaldehyde and ethylenediamine are reacted together in 1:1 or 2:1 mole ratios in the presence of a platinum group metal (such as Ni, Ru or Pd) and a reducing agent (such as hydrogen) to yield 1 and 2 respectively.

EXAMPLE 2

N,N'-Bis(chloroacetyl)-N-benzylethylenediamine 3

(a) A 250 mL flask was charged with 1 (7.53 g, 50.1 mmol), 55 mL CH$_2$Cl$_2$, 16.6 g (120 mmol) K$_2$CO$_3$ and 60 mL of water. The resulting 2 phase solution was cooled to ca. 5° C. A solution of chloroacetylchloride (10 mL, 126 mmol) in 50 mL of $CH_2Cl_2$ was added drop-wise to the cooled solution while maintaining the temperature at 5° to 10° C. After warming the solution to ambient temperature the aqueous solution was separated and washed with $CH_2Cl_2$ (2×25 mL). The combined $CH_2Cl_2$ solutions were washed with water and concentrated. The resulting oil 3 was used directly in xample 4(a). $^{13}C$ NMR ($CDCl_3$):δ 38.09, 41.04, 42.38, 45.21, 51.73, 126.30, 127.70, 128.77, 135.30, 166.66, 168.33.

(b) 3.5 kg of $K_2CO_3$ was dissolved in 10 liters of water at ambient temperature. To this was added 10.6 liters of $CH_2Cl_2$ and 1.6 kg of 1. The mixture was cooled to 5° C. A separate solution was made consisting of 3.0 kg of chloroacetylchloride in 12.8 liters of $CH_2Cl_2$. The chloroacetylchloride solution was slowly added to the cooled mixture while maintaining the temperature at 5° to 10° C. After completing the addition, the mixture was warmed to ambient temperature. The $CH_2Cl_2$ phase was separated and the water phase was washed with additional $CH_2Cl_2$. The combined $CH_2Cl_2$ phases were washed with water, then used directly in Example 4(b). (The volume of the $CH_2Cl_2$ solution was 30 liters).

EXAMPLE 3

N,N'-bis(bromoacetyl)-N-benzylethylenediamine 4

A 2-L, 3-neck, round bottom flask equipped with an overhead stirrer, an addition funnel and a thermometer was charged with 69.86 g (0.444 mol). of bromoacetyl chloride, 750 mL of $CH_2Cl_2$, and 62 g (0.449 mol) of $K_2CO_3$. The mixture was chilled to between 5° and 10° C. before slowly adding 28.99 g (0.193 mol) of 1 in 250 mL of $CH_2Cl_2$ while maintaining the temperature at ca.10° C. The reaction mixture was stirred for ½ hour at 10° to 15° C. Water (250 mL) was then carefully added to the chilled mixture (5° to 10° C.). The organic layer was separated. The aqueous layer was washed with 300 mL of $CH_2Cl_2$, and the organic layers were combined and extracted with 2×300 mL deionized water. The organic layer was concentrated and the product 4 used directly in Example 4(c). $^{13}C$ NMR ($CDCl_3$): δ25.99, 28.74, 38.46, 45.10, 52.26, 126.30, 128.13, 129.14, 135.36, 166.30, 168.73.

EXAMPLE 4

1,4,7-tribenzyl-1,4,7,10-tetraaza-2,9-dioxocyclododecane 5

(a) A 2 liter flask equipped with a nitrogen inlet and a reflux condenser was charged with the product 3 from Example 2(a) dissolved in 300 mL acetonitrile (ACN). 2 (10.2 g, 42 mmol), $Na_2CO_3$ (70 g, 0.66 mol), and an additional 625 mL ACN were added to the flask. The mixture was refluxed for 3 days. The mixture was cooled to ambient temperature and the bulk of the ACN was removed under reduced pressure. To the residue was added 300 mL $CH_2Cl_2$ and water. The organic layer was separated. The aqueous layer was washed with additional $CH_2Cl_2$. The organic layers were combined and washed with deionized water. The organic layer was concentrated. The product was precipitated with ethyl acetate, collected by filtration and washed with fresh ethyl acetate. The yield of 5 (m/e=471) was 67%.

(b) 21 liters of $CH_2Cl_2$ were removed from the product of Example 2(b) by atmospheric distillation. 21 liters of acetonitrile (ACN) was added and the distillation continued until the head temperature was 82° C. 120 liters of ACN, 6.7kg of anhydrous $K_2CO_3$, and 2.3 liters of 2 were added. The mixture was heated to reflux for 6 hours. 120 to 130 liters of solvent was removed by distillation. To the remainder were added 27 liters of water. The mixture was cooled below 40° C. and 53 liters of $CH_2Cl_2$ was added. The phases were separated and the water was back-extracted with 8 liters of $CH_2Cl_2$. The organic phases were combined and 50 L of $CH_2Cl_2$ was removed by distillation. 21 liters of ethyl acetate was added and an additional 11 liters of $CH_2Cl_2$ was removed by distillation. The solution was cooled to 20° C. and the precipitated product was filtered, washed with ethyl acetate and dried to yield 5 (m/e=471). The yield was 2.5 kg(53% yield).

(c) A 2-L, 3-neck, round bottom flask equipped with an overhead stirrer, a reflux condenser and a thermometer was charged with 375 mL dimethylformamide (DMF) and 50 g of $K_2CO_3$. The mixture was heated to 50° C. 46.3 g (0.193 mols) of N,N'-dibenzylethylenediamine diluted to 125 mL with DMF and the product 4 from Example 3 diluted to 125 mL with DMF were added to the warm potassium carbonate suspension in DMF over 6 hour. The resulting suspension was heated for 6 hr. About ½ of the DMF was removed by distillation at reduced pressure. 300 mL of deionized water was added to the solution followed by 300 mL $CH_2Cl_2$. The material was transferred into a 2-L separatory funnel, and the organic layer was separated. The aqueous layer was washed with 100 mL $CH_2Cl_2$ and the organic layers were combined and washed with 2×150 mL of deionized water. The organic layer was concentrated under reduced pressure. The product 5 was precipitated with ethyl acetate, collected by filtration and washed with fresh ethyl acetate. The yield of 5 (m/e= 471) was 47%.

EXAMPLE 5

Tribenzylcyclen 6

(a) A 1-L, 3-neck round bottom flask equipped with a reflux condenser, an overhead stirrer and a nitrogen inlet was charged with 10.0 g (0.021 mols) of 5 and 72 mL of THF. The mixture was stirred under nitrogen. After cooling to 5° to 10° C., 176 mL of 1.0M $BH_3$. THF was added to the suspension [note: $H_2$ was evolving during the addition of the $BH_3$]. The resulting solution was refluxed for 12 hours under nitrogen. A white solid forms during the course of the reaction. The mixture was cooled to ca. 25° C. before carefully quenching the remaining $BH_3$ with 64 mL of $H_2O$ (3.55 mols) [note: substantial $H_2$ was evolved during the quench of the $BH_3$]. After removing 236 mL of THF under reduced pressure, 25 mL of 12M HCl (0.3 mol) was carefully added to the solution [note: $H_2$ seemed to be evolved during the addition of HCl. The solution warmed to ca. 30° C. and foamed]. The cloudy, acidic mixture was refluxed 3 hours to afford a clear, colourless solution. After cooling the solution to ambient temperature the pH was adjusted to ca. 14 with 25 mL of 50% aqueous NaOH. The product was extracted with 120 mL of $CH_2Cl_2$. The aqueous phase was separated and washed with an additional 85 mL of $CH_2Cl_2$. The combined organic phases were washed with 2×50 mL of $H_2O$. The bulk of the $CH_2Cl_2$ was removed under reduced pressure to give 9.4 g of crude product 6. This solid was dissolved in ca. 40 mL of boiling acetonitrile. The solution was slowly cooled to 0° C. The resulting precipitate was collected by filtration and dried to afford 6.1 g of a colourless crystalline product 6 (m/e=443). The yield based of 6 was 65% based on 5.

(b) A 1-L, 3-neck round bottom flask equipped with a reflux condenser, an overhead stirrer, and a nitrogen inlet was charged with 10.0 g (0.021 mols) of 5, 7.45 g (0.197 mols) $NaBH_4$, and 300 mL of THF. The suspension was stirred under nitrogen. In a separate flask 22 g (0.23 mols) of methane sulphonic acid was dissolved in 100 mL of cooled THF [note: the dissolution of the acid in THF is exothermic]. The acid solution was slowly added to the borohydride suspension with stirring [note: $H_2$ was evolved during the addition of the $BH_3$. The suspension thickens during the acid addition, but thins somewhat as the last of the acid is added]. The resulting suspension was refluxed for 12 hours under nitrogen. The mixture was cooled to ca. 25° C. before carefully quenching the remaining $BH_3$ with 50 mL of $H_2O$ (2.87 mols) [note: substantial $H_2$ was evolved during the quench of the $BH_3$]. After removing ½ of the THF under reduced pressure an additional 100 mL water was added. The bulk of the remaining THF was removed by distillation before 50 mL of 12M HCl (0.6 mols) was carefully added to the solution. The acidic mixture was refluxed 3 hours. After cooling the solution to ambient temperature the pH was adjusted to 12 to 13 with 50% aqueous NaOH. The product was extracted with 2×125 mL of $CH_2Cl_2$. The combined organic phases were washed with 3×125 mL of $H_2O$. The bulk of the $CH_2Cl_2$ was removed under reduced pressure to give crude product. This solid was dissolved in ca. 35 mL of boiling acetonitrile. The solution was slowly cooled to −5° C. The resulting precipitate was collected by filtration and dried to afford 7.1 g of a colourless crystalline tribenzylcyclen 6 (m/e=443). The yield was 75% based on 5. The sample is clean by $^1H$ and $^{13}C$ NMR.

EXAMPLE 6

1,14-dibromo-2,13-dioxo-3,12-diaza-6,9-dioxa-tetradecane 7

A 500 mL round bottom flask equipped with an addition funnel, a thermometer, and $N_2$ inlet was charged with 24.8 g (160 mmol) of bromoacetyl chloride, 300 mL of $CH_2Cl_2$, and 25 g of $K_2CO_3$. The suspension was cooled to 5° to 10° C. in an ice bath before 10.1 g (68 mmol) of 2,2'-(ethylenedioxy)diethylamine in 100 mL of $CH_2Cl_2$ was added drop-wise with cooling (exothermic). The reaction mixture was allowed to stir at ambient temperature for 1 hour before adding 250 mL of deionized water. The organic layer was separated from the aqueous layer. The aqueous layer was washed with 2×200 mL of $CH_2Cl_2$. All organic layers were combined and washed with 3×250 mL of deionized water. As the organic layer was concentrated to dryness the thick oil solidified to a colourless solid. The crude solid 7 was recrystallized from hot ethanol. The resulting crystalline solid was collected, dried and characterised by $^1H$ and $^{13}C$ NMR and mass spectrometry (m/e=391). The yield of 7 was 80%.

EXAMPLE 7

1,14-bis(4,7,10-tribenzyl-1,4,7,10-tetraazacyclododecyl)-2,13-dioxo-3,12-diaza-6,9-dioxatetradecane 8

7 was reacted with two equivalents of tribenzylcyclen as follows. A 100 mL round bottom flask equipped with a reflux condenser was charged with 1.5 g (3.4 mmols) of tribenzylcyclen 6, 0.661 g (1.7 mmols) of 7 and 0.39 g (3.4 mmols) of tetramethylguanidine (TMG) in 50 mL of $CH_2Cl_2$. The reaction mixture was stirred for 6 hours at 55° C., then overnight at ambient temperature. The bulk of the DMF was removed under vacuum. Work-up from $CH_2Cl_2$/$H_2O$ afforded the product as a thick light yellow oil. $^1H$ NMR, $^{13}C$ NMR and mass spectroscopy data (m/e=1114) were consistent with pure product 8 contaminated only with residual DMF.

EXAMPLE 8

1,14-bis-(1,4,7,10-tetraazacyclododecyl)-2,13-dioxo-3,12-diaza-6,9-dioxatetradecane 9

(a) A 100 mL round bottom flask equipped with a reflux condenser and $N_2$ inlet was charged with 1.09 g (0.98 mmol) of 8, 30 mL of ethanol and 1.133 g of ammonium formate. The flask was purged through with nitrogen for 15 min and 216 mg of 10% Pd/C was added. The reaction solution was refluxed overnight. The mixture was filtered through a bed of Celite and the filtrate was concentrated to a slightly yellow oil. $^1H$ NMR, $^{13}C$ NMR, and mass spectroscopy data (m/e=573) were consistent with 9. The yield of 9 was essentially quantitative.

(b) A 100 mL Autoclave pressure reactor was charged with 9.2 g (8.3 mmol) of 8, 50 mL of ethanol and 3 g of 10% Pd/C. The reactor was pressurized to 220 psig with hydrogen for 3 hours at 80° C. The mixture was filtered and the filtrate was concentrated to a slightly yellow oil. $^1H$ NMR, $^{13}C$ NMR, and mass spectroscopy data were consistent with 9. The yield of 9 was essentially quantitative.

EXAMPLE 9

1,14-bis-(4,7,10-tris(carboxymethyl-benzylester)-1,4,7,10-tetraazacyclododecyl)-2,13-dioxo-3,12-diaza-6,9-dioxatetradecane 10

A 250 mL round bottomed flask equipped with a reflux condenser was charged with 1.84 g (3.2 mmol) of 9, 100 mL DMF, 5.99 g (25.7 mmols) of benzyl bromoacetate, and 2.95 g (25.7 mmols) of TMG. The reaction mixture was heated to 55° C. for 5 hours. The mixture was concentrated under reduced pressure to about ½ its original volume. Work-up of the reaction from $CH_2Cl_2$/$H_2O$ afforded the product 10 as a yellow oil contaminated with residual DMF. $^1H$ NMR, $^{13}C$ NMR and mass spectroscopy data (m/e=1461) were consistent with 10.

EXAMPLE 10

1,14-bis-(4,7,10-tris(carboxymethyl)-1,4,7,10-tetraazacyclododecyl)-2,13-dioxo-3,12-diaza-6,9-dioxatetradecane 11

A 100 mL Autoclave pressure reactor was charged with 4.7 g (3.2 mmol) of 10, 50 mL of 50% aqueous THF and 1 g of 10% Pd/C. The reactor was pressurised to 220 psig with hydrogen for 3 hours at 80° C. The mixture was filtered and the filtrate was concentrated to a slightly yellow glassy solid. $^1H$ NMR, $^{13}C$ NMR, and mass spectroscopy data (m/e=922) were consistent with 11. The yield of 11 was essentially quantitative.

EXAMPLE 11

[1, 14-bis-(4,7,10-tris(carboxymethyl)-1,4,7,10-tetraazacyclododecyl)-2,13-dioxo-3,12-diaza-6,9-dioxatetradecane] Gd (III) chelate 12

To a flask was added 3.44 g (3.7 mmol) of 11 and 200 mL deionized water. 3.019 g (7.5 mmol) of Gadolinium acetate was added at 40° C. Removal of the solvent yielded 4.65 g of white solid 12. Anal. Calcd. (found) for $C_{38}H_{62}N_{10}O_{16}Gd_2 \cdot 4.75H_2O$: C 34.71(34.99); H 5.48(5.38); N 10.65(10.77); Gd 23.92(23.88).

EXAMPLE 12

1,4,7-tetraazacyclododecane 13 (cyclen)

Tribenzylcyclen (2.0 g, 4.5 mmol), ethanol (50 mL), and 10% Pd on carbon (1.0 g) were loaded into a 100 mL Autoclave pressure reactor. The reactor was pressurized to 100 psig with hydrogen for 3 hours at 80° C. The mixture was filtered to remove the catalyst and the filtrate was concentrated to afford pure 13 in essentially quantitative yield. $^{13}$C NMR ($D_2O$): δ 46.30

EXAMPLE 13

1,4,7-tris (carboxymethyl-tert-butyl ester) -1,4,7,10-tetraazacyclododecane 14

To a mixture of 35 g cyclen (0.20 mols) and 50 g sodium acetate (0.61 mols) in 600 mL dimethylacetamide (DMA) was added a solution of tert-butyl bromoacetate (118.9 g, 0.61 mols) in 150 mL DMA. After stirring the mixture for 19 days at ambient temperature the precipitated product was collected by filtration. The filtrate was concentrated to afford a second crop of product. The combined crops (118.5 g) were dissolved in chloroform and washed with water. The chloroform was removed under reduced pressure. The addition of ethyl acetate to the yellow oil gave a white solid which was collected by filtration and washed with ether. The yield of 14 was 67.4 g (56%). $^{13}$C NMR of 14.HBr ($CDCL_3$): δ 28.08, 28.11, 47.41, 49.11, 51.25, 58.06, 80.97, 81.57, 169.52, 170.40.

EXAMPLE 14

1,4,7-tris(carboxymethyl)-1,4,7,10-tetraazacyclododecane 15

To ca. 400 mL of trifluoroacetic acid/$CHCl_3$ (1:1) was added 0.034 mols of 14. After stirring for 1 hour at ambient temperature the solvents were removed under reduced pressure. This process was repeated 3 times to afford a yellow oil. The oil was mixed with methanol (15 mL) and diluted to 1 liter with acetone. The precipitated white solid was collected by filtration and dried in vacuo to afford 11.75 g (99%) of 15. $^{13}$C NMR ($D_2O$): δ 43.00, 48.48, 49.67, 52.32, 53.94, 56.92, 170.77, 175.35.

EXAMPLE 15

1,4,7-tris (carboxymethyl)-10-(2-hydroxypropyl)-1,4,7,10-tetraazacyclododecane 16

To a solution of 194.0 g (0.56 mol) of 15 in 450 mL of water is added sufficient NaOH to adjust the pH to 12.0 to 12.5 (the temperature is maintained below 30° C. during the addition). Propylene oxide (65 g, 1.12 mols) is added to the basic solution. After 6 hours at ambient temperature the excess propylene oxide and solvent is removed under reduced pressure. The product is precipitated from a minimal amount of methanol to afford 16 in 96% yield.

EXAMPLE 16

[1,4,7-tris(carboxymethyl)-10-(2-hydroxypropyl)-1,4,7,10-tetraazacyclododecane] gadolinium 17

To a solution of 20.22 g (0.05 mol) of 16 in 100 mL of water is added 9.54 g (0.0263 mol) of $Gd_2O_3$. The suspension is stirred for 20 hours at 95° C. The solvent is removed in vacuo and the product is recrystallized from methanol/acetone to afford 17 as a white solid in 56% yield.

EXAMPLE 17

[1,4,7-tris(carboxymethyl)-10-(10-(3,5-dicarboxyphenyl)-decyl)-1,4,7,10-tetraazacyclododecane] 18

A round bottom flask equipped with a reflux condenser is charged with 0.2 mols of tribenzylcylen, 0.2 mols of 10-(3,5-dicarboxyphenyl)-1-bromodecane, 1 liter of DMF and 0.2 mols of tetramethylguanidine (TMG). The reaction mixture is stirred for ca. 12–16 hours at 60°–65° C. The bulk of the DMF is removed under vacuum. Work-up from $CH_2Cl_2$/$H_2O$ affords the alkylated tribenzylcyclen intermediate.

The alkylated tribenylcyclen intermediate is debenzylated as follows: A 100 mL Autoclave pressure reactor is charged with ca. 10 mmol of substrate, 50 mL of ethanol and 3 g of 10% Pd/C. The reactor is pressurized to 100–200 psig with hydrogen for 3 hours at 80° C. The mixture is filtered to remove the catalyst and the filtrate is evaporated to give 1-[10-(3,5-dicarboxyphenyl)-decyl]-1,4,7,10-tetraazacyclododecane.

To an aqueous solution of 1-[10-(3,5-dicarboxyphenyl) decyl]-1,4,7,10-tetraazacyclododecane (0.16 mols in 500 mL water) is added an aqueous solution of sodium chloroacetate (0.71 mols sodium chloroacetate in 68 mL of water). This solution is stirred at 80° C. overnight while maintaining the pH at 9–10. After cooling to ambient temperature the pH of the solution is adjusted to 2.5 with aqueous HCl. The resulting precipitate is collected by filtration, washed with acetone, and dried in vacuo to afford 18.

EXAMPLE 18

[1,4,7-tris(carboxymethyl)-10-(2-(1,3,4-trihydroxybutyl)]-1,4,7,10-tetraazacyclododecane] 19

A round bottom flask equipped with a reflux condenser is charged with i liter of acetonitrile, 0.2 mols of tribenylcyclen and 0.2 moles of 1,4-dihydroxy-2-butene oxide. The reaction mixture is stirred for ca. 12–16 hours at 60°–65° C. The bulk of the acetonitrile is removed under vacuum. Work-up from $CH_2Cl_2$/$H_2O$ affords the trihydroxybutyl tribenzylcyclen intermediate.

The trihydroxybutyl tribenzylcyclen intermediate is debenzylatyed as follows: A 100 mL Autoclave pressure reactor is charged with ca.10 mmol of substrate, 50 mL of ethanol and 3 g of 10% Pd/C. The reactor is pressurized to 100–200 psig with hydrogen for 3 hours at 80° C. The mixture is filtered to remove the catalyst and the filtrate is evaporated to give 1-[2-(1,3,4-trihydroxybutyl)]-1,4,7,10-tetraazacyclododecane To an aqueous solution of 1-[2-(1,3,4-trihydroxybutyl)]-1,4,7,10-tetraazacyclododecane (0.16 mols in 500 mL water) is added an aqueous solution of sodium chloroacetate (0.71 mols sodium chloroacetate in 68 mL of water). This solution is stirred at 80° C. overnight while maintaining the pH at 9–10. After cooling to ambient temperature the pH of the solution is adjusted to 2.5 with aqueous. HCl. The resulting precipitate is collected by filtration, washed with acetone, and dried in vacuo to afford 19.

EXAMPLE 19

1-benzyl-1,4,7,10-tetraaza-2,9-dioxocyclododecane 20

A 2-L, 3-neck, round bottom flask equipped with an overhead stirrer, a reflux condenser, and a thermometer is charged with 375 mL dimethylformamide (DMF) and 50 g of $K_2CO_3$. The mixture is heated to 50° C. Ethylene diamine (0.2 mols) diluted to 125 mL with DMF and the product 4 from Example 3 diluted to 125 mL with DMF are added to the warm potassium carbonate suspension in DMF over ½ hour. The resulting suspension is heated for 6 hours. About ½ of the DMF is removed by distillation at reduced pressure. 300 mL of deionized water is added to the solution followed by 300 mL $CH_2Cl_2$. The material is transferred into a 2-L separatory funnel, and the organic layer is separated. The aqueous layer is washed with 100 mL $CH_2Cl_2$, and the organic layers are combined and washed with 2×150 mL of deionized water. The organic layer is concentrated under reduced pressure. The product 20 is precipitated with ethyl acetate, collected by filtration and washed with fresh ethyl acetate.

EXAMPLE 20

N-Benzylcyclen 21

A 1-L, 3-neck round bottom flask equipped with a reflux condenser, an overhead stirrer, and a nitrogen inlet is charged with 10.0 g (0.021 mols) of 20 and 72 mL of THF. The mixture is stirred under nitrogen. After cooling to 5°–10° C., 176 mL of 1.0M $BH_3$. THF is added to the suspension. The resulting solution is refluxed for 12 hours under nitrogen. A white solid forms during the course of the reaction. The mixture is cooled to ca. 25° C. before carefully quenching the remaining $BH_3$ with 64 mL of $H_2O$ (3.55 mols). After removing 236 mL of THF under reduced pressure, 25 mL of 12M HCl (0.3 mols) are carefully added to the solution. The cloudy, acidic mixture is refluxed 3 hours to afford a clear, colourless solution. After cooling the solution to ambient temperature the pH is adjusted to ca. 14 with 25 mL of 50% aqueous NaOH. The product is extracted with 120 mL of $CH_2Cl_2$. The aqueous phase is separated and washed with an additional 85 mL of $CH_2Cl_2$. The combined organic phases are washed with 2×50 mL of $H_2O$. The bulk of the $CH_2Cl_2$ is removed under reduced pressure to give 21.

We claim:

1. A process for the production of 1,4,7-tris (carboxymethyl)-1,4,7,10-tetraazacyclododecane chelating agents or 1,4,7-tris(carboxymethyl)-1,4,7,10-tetraazacyclododecane analog chelating agents, said process comprising:

(1) (a) reacting a diamine of formula XII $$Z_1NHCHR_1CHR_1NH_2 \quad (XII)$$

with a diamine of formula XIII $$YNZ_2CHR_1CHR_1NHY \quad (XIII)$$

where $R_1$ is (i) hydrogen, (ii) a $C_{1-6}$ alkyl group optionally substituted by hydroxy, alkoxy or carboxy groups, or (iii) an aralkyl group having 1 to 6 carbon atoms in the alkyl moiety and optionally substituted in the aryl moiety by alkyl, alkoxy, hydroxy or isothiocyanate groups; Y is $CH_2COLv$ or $COCH_3Lv$ where Lv is a leaving group; and one of $Z_1$, and $Z_2$ is hydrogen and the other is a benzyl group, and (b) where necessary reducing the cyclic dione thus produced to yield N-benzyl-cyclen;

(2) reacting the N-benzyl-cyclen to introduce acid groups at the unsubstituted ring nitrogens;

(3) debenzylating the N-acid substituted product; and (4) if desired, N-alkylating the debenzylated product.

2. A process as claimed in claim 1 wherein in step (4) the debenzylated product is N-alkylated to introduce a hydroxyalkyl group.

3. A process for the production of 1,4,7-tris (carboxymethyl)-1,4,7,10-tetraazacyclododecane chelating agents or 1,4,7-tris(carboxymethyl)-1,4,7,10-tetraazacyclododecane analogue chelating agents, said processing comprising:

(1) (a) reacting a triamine of formula (XIV)

$$Z_1NHCHR_1CHR_1NZ_2CHR_1CHR_1NH_2 \quad (XIV)$$

with a monoamine of formula XIV or XVI $$Z_3N(CH_2COLv)_2 \quad (XV)$$

$$Z_3N(CHR_1CHR_1Lv)_2 \quad (XVI)$$

where $R_1$ is hydrogen, a $C_{1-6}$ alkyl group optionally substituted by hydroxy, alkoxy or carboxy groups or an aralkyl group having 1 to 6 carbon atoms in the alkyl moiety and optionally substituted in the aryl moiety by alkyl, alkoxy, hydroxy or isothiocyanate groups; Lv is a leaving group; one of $Z_1$, $Z_2$ and $Z_3$ is a benzyl group and the other two are hydrogen atoms, and (b) where necessary reducing the cyclic dione thus produced to yield N-benzyl-cyclen;

(2) reacting the N-benzyl-cyclen to introduce acid groups at the unsubstituted ring nitrogens;

(3) debenzylating the N-acid substituted product; and (4) if desired, N-alkylating the debenzylated product.

4. A process as claimed in claim 3 wherein step (4) the debenzylated product is N-alkylated to introduce a hydroxyalkyl group.

* * * * *